US006916607B2

(12) United States Patent
Rosinski-Chupin et al.

(10) Patent No.: US 6,916,607 B2
(45) Date of Patent: *Jul. 12, 2005

(54) PEPTIDES AND POLYPEPTIDES DERIVED FROM THE SUBMAXILLARY GLAND OF THE RAT CORRESPONDING POLYCLONAL AND MONOCLONAL ANTIBODIES CORRESPONDING HYBRIDOMAS AND USES OF THESE PRODUCTS FOR DIAGNOSIS FOR DETECTION OR THERAPEUTIC PURPOSES

(75) Inventors: Isabelle Rosinski-Chupin, Versailles (FR); Diana Tronik, Meudon (FR); François Rougeon, Piogny la Foret (FR); Nabil Seidah, Montreal (CA)

(73) Assignee: Institute Pasteur, Paris (FR)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/386,850

(22) Filed: Aug. 31, 1999

(65) Prior Publication Data

US 2003/0170620 A1 Sep. 11, 2003

Related U.S. Application Data

(62) Division of application No. 08/476,120, filed on Jun. 7, 1995, now Pat. No. 6,025,143, which is a continuation of application No. 08/153,277, filed on Nov. 17, 1993, now Pat. No. 5,859,189, which is a continuation of application No. 07/499,276, filed as application No. PCT/FR89/00523 on Oct. 11, 1989, now abandoned.

(30) Foreign Application Priority Data

Oct. 11, 1988 (FR) ............................................. 88 13353

(51) Int. Cl.[7] ........................... C12Q 1/68; G01N 33/50
(52) U.S. Cl. ............................................. 435/6; 436/63
(58) Field of Search .............................. 435/6; 436/63; 536/23.1, 23.5, 23.51

(56) References Cited

U.S. PATENT DOCUMENTS

| 4,474,893 A | 10/1984 | Reading |
| 4,596,790 A | 6/1986 | Trygstad et al. |
| 4,699,877 A | 10/1987 | Cline et al. |
| 4,722,899 A | 2/1988 | Hamaoka et al. |
| 4,886,747 A | * 12/1989 | Derynck et al. |

FOREIGN PATENT DOCUMENTS

| EP | 277313 | * 8/1988 |
| WO | 83/039972 | 11/1983 |

OTHER PUBLICATIONS

Accession No. A11237, Dec. 10, 1993.*
Accession No. AAQ03301, 1989.*
Flanders et al., *Biochemistry*, 27:739–746 (1988).
Dunn et al., *J. Biol. Chem.*, 253(20):7269–7275 (1978).
Kendaich et al., *J. Biol. Chem.*, 213(34):18313–17 (1988).
Simpson et al., *Euro. J. Biochem.*, 153:629–637 (1985).
Dicou et al., *Proc. Natl. Acad. Sci. USA*, 83:7084–7088 (1986).
Chupin et al., *DNA and Cell Biology*, 9(8):553–559 (1990).
Chupin et al., *PNAS*, 85:8553–8557 (1988).
*Chemical Abstracts*, 114:95812a (1991).
Seaver, *Genetic Engineering News*, 14(14):10, 21 (1994).
Schaffhausen, *Hybridoma technology in the Biosciences and Medicine*, 21:355–373 (1985).
Tanaka et al., *Proc. Natl. Acad. Sci. USA*, 82:3400–3404 (1985).
Geysen et al., *Proc. Natl. Acad. Sci. USA*, 81:3998–4002 (1994).
Seiver et al., *Clin. Chem.*, 27(11):1797–1806 (1981).
Grouselle et al., *Neuropeptides*, 17:155–162 (1990).
Rougeot et al., *Eur. J. Biochem.*, 219:765–773 (1994).
Montoya et al., *Endo*, 96(6):1413–1418 (1975).
Gregory et al., *Biochimica et Biophysica Acta*, 133:319–332 (1967).
Ezan et al., *INIST CNRS*, Chapter 6, pp. 143–179 (1998).
Lombardi et al., *Acta Endocrinologica*, 87:70–79 (1978).

* cited by examiner

*Primary Examiner*—Karen A. Canella
(74) *Attorney, Agent, or Firm*—Burns, Doane, Swecker & Mathis, L.L.P.

(57) ABSTRACT

The present invention relates to peptides and polypeptide derived from the submaxillary gland of the rat. In particular, the present invention discloses a purified peptide of formuls: X-His-Asn-Pro-Y in which X represents a Gln or Pro-Glu residue and Y represents an OH group or residue of a basic amino acid. The present invention also relates to corresponding polyclonal and monoclonal antibodies as well as corresponding hybridomas. The products of the present invention are useful for therapeutic, diagnosis and detection purposes.

2 Claims, 1 Drawing Sheet

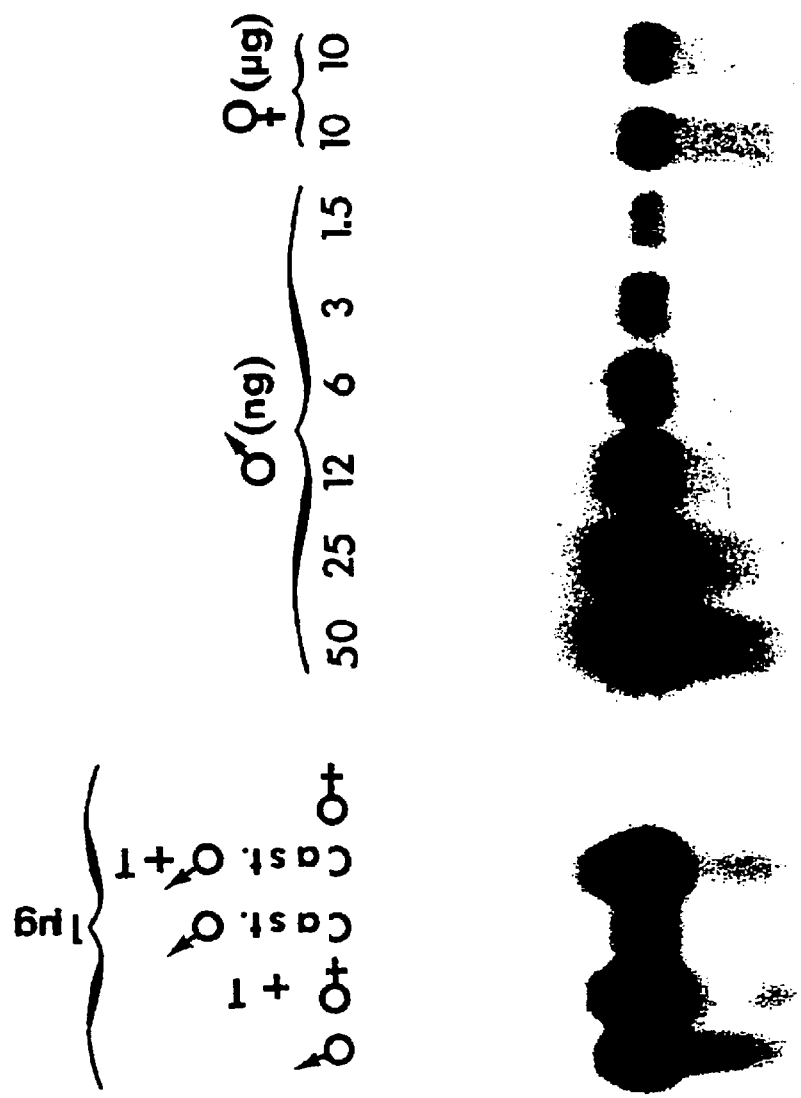

US 6,916,607 B2

PEPTIDES AND POLYPEPTIDES DERIVED FROM THE SUBMAXILLARY GLAND OF THE RAT CORRESPONDING POLYCLONAL AND MONOCLONAL ANTIBODIES CORRESPONDING HYBRIDOMAS AND USES OF THESE PRODUCTS FOR DIAGNOSIS FOR DETECTION OR THERAPEUTIC PURPOSES

CROSS REFERENCE TO RELATED APPLICATIONS

This application is a divisional of application Ser. No. 08/476,120, filed on Jun. 7, 1995, now U.S. Pat. No. 6,025,143, which is a continuation of application Ser. No. 08/153,277, filed on Nov. 17, 1993, now U.S. Pat. No. 5,859,189, which is a continuation of application Ser. No. 07/499,276, filed on Jul. 19, 1990, now abandoned, which is a § 371 application of International Application No. PCT/FR89/00523, filed on Oct. 11, 1989.

The present invention relates to novel peptides which are maturation products of polypeptide secreted by the submaxillary gland of the rat and analogues of these peptides.

Many polypeptide having defined biological properties are synthesized in large quantities in the submaxillary gland (SMG) of rodents, and in particular in the SMG of the mouse. These proteins, comprising the nerve growth factor (NGF), the epidermal growth factor (EGF) and renin, have a certain number of properties in common. They are all synthesized in the same type of cell, namely the cells of the convoluted tubules GCT (granular convoluted tubular), in response to various hormonal stimuli, in particular to androgens. Furthermore, it is possible to observe the presence of these secretory proteins in the saliva of the mouse, and they are synthesized in the form of precursors which become active after maturation processes which may involve proteases of the kallikrein type. Some of these proteases of the kallikrein type are also synthesized in the SMG under the control of androgens.

SUMMARY OF THE INVENTION

Attempts at the characterization of the genes controlled by the androgens in the SMG of the rat have led the inventors to analyse the electrophoretic profile of the in vitro translation products of the mRNA of this tissue.

A specific mRNA of the submaxillary gland of the male rat has been isolated. This mRNA corresponds to a polypeptide which has been designated SMR1. This polypeptide gives maturation products with physiological activity. The present invention relates mainly to these peptides and to other peptides having similar properties.

BRIEF DESCRIPTION OF TILE DRAWINGS

FIG. 1A shows mRNAs coding for SMR1 in the SMG of male rats, female rats treated with testosterone, castrated male rats, castrated male rats treated with testosterone and female rats.

FIG. 1B shows mRNAs coding for SMR1 from various amounts of RNA from the SMG of male rats and female rats.

DETAILED DESCRIPTION OF THE INVENTION

Thus the subject of the present invention is peptides of formula:

X-His-Asn-Pro-Y            I in which:

X represents a glutamine (Gln) or pyroglutamic acid (pyro-Glu) residue,

Y represents a OH group or a residue of a basic amino acid.

The basic amino acids may be lysine or arginine.

More specifically, the subject of the present invention is peptides of formula:

Gln-His-Asn-Pro(SEQ ID NO: 1) II
    pyro-Glu-His-Asn-Pro (SEQ ID NO: 2) III
    Gln-His-Asn-Pro-Arg (SEQ ID NO: 3) IV
    pyro-Glu-His-Asn-Pro-Arg (SEQ ID NO: 4) V
    Gln-His-Asn-Pro-Lys (SEQ ID NO: 5) VI
    pyro-Glu-His-Asn-Pro-Lys (SEQ ID NO: 6) VII

```
 1
Met Lys Ser Leu Tyr Leu Ile Phe Gly Leu Trp Ile
                                     20
Leu Leu Ala Cys Phe Gln Ser Gly Glu Gly Val Arg
                         30
Gly Pro Arg Arg Gln His Asn Pro Arg Arg Gln Gln
                 40
Asp Pro Ser Thr Leu Pro His Tyr Leu Gly Leu Gln
         50                                   60
Pro Asp Pro Asn Gly Gly Gln Ile Gly Val Thr Ile
                                             70
Thr Ile Pro Leu Asn Leu Gln Pro Pro Arg Val Leu
                                         80
Val Asn Leu Pro Gly Phe Ile Thr Gly Pro Pro Leu
                             90
Val Val Gln Gly Thr Thr Glu Tyr Gln Tyr Gln Trp
                     100
Gln Leu Thr Ala Pro Asp Pro Thr Pro Leu Ser Asn
             110                                 120
Pro Pro Thr Gln Leu His Ser Thr Glu Gln Ala Asn
                                     130
Thr Lys Thr Asp Ala Lys Ile Ser Asn Thr Thr Ala
                                 140
Thr Thr Gln Asn Ser Thr Asp Ile Phe Glu Gly Gly
Gly Lys
```

Another subject of the present invention is monoclonal and polyclonal antibodies directed against the peptides and the polypeptide according to the invention.

Another subject of the present invention is hybridomas producing monoclonal antibodies directed against the peptides I to VII and the polypeptide according to the invention.

Another subject of the present invention is a procedure for the assay or detection of the peptides and polypeptide according to the invention in tissues and biological fluids which comprises the utilization of monoclonal or polyclonal antibodies according to the invention.

For this purpose, it is possible to utilize in particular a method of the RIA type using a peptide labelled by a radioisotope, and the competition between this peptide and the peptide to be assayed (Niswender G. D. et al; Proc. Soc. Exp. Biol. 128, 807, 1968). It is also possible to utilize a method of the ELISA type using, for example, a peptide bound to a support and the competition between this peptide and the peptide to be assayed for antibodies prepared against this peptide. The antibodies retained by the peptide bound to the support are detected by antibodies directed against the former and linked to an enzyme (method derived from Avromeas J. and Guilbert B, C.R. Acad. Sci. Paris 1971, 273, 2305).

The peptides according to the present invention may be prepared in a standard manner by peptide synthesis in liquid or solid phase by successive couplings of the different amino acid residues to be incorporated (from the N-terminal end toward the C-terminal end in liquid phase, or from the C-terminal end to the N-terminal end in solid phase) and the N-terminal ends and the reactive side chains of which are blocked beforehand by standard groupings.

For this synthesis on solid phase it is possible to utilize in particular the technique described by Merrifield, in the article entitled "Solid phase peptide synthesis" (J. Am. Chem. Soc., 85, 2149–2154).

In order to produce a peptide chain according to the Merrifield procedure, recourse is had to a very porous polymeric resin, to which the first C-terminal amino acid of the chain is bound. This amino acid is bound to the resin through the intermediary of its carboxyl group and its amino function is protected, for example by the t-butoxycarbonyl group.

When the first C-terminal amino acid is thus bound to the resin, the protecting group is removed from the amine function by washing the resin with an acid. In the case in which the protecting group for the amine function is the t-butoxycarbonyl group, it may be removed by treatment of the resin with the aid of trifluoroacetic acid.

The second amino acid, which provides the second residue of the desired sequence, is then coupled to the deprotected amine function of the first C-terminal amino acid bound to the chain. Preferably, the carboxyl function of this second amino acid is activated, for example, by means of dicyclohexylcarbodiimide, and the amine function is protected, for example, by the t-butoxycarbonyl.

In this way, the first part of the desired peptide chain is obtained which contains two amino acids and the terminal amine function of which is protected. As previously, the amine function is deprotected and it is then possible to proceed to the attachment of the third residue under similar conditions to those for the addition of the second C-terminal amino acid.

In this manner, the amino acids which will constitute the peptide chain are attached one after the other to the amine group, deprotected beforehand each time, of the portion of the peptide chain already formed and which is attached to the resin.

When the whole of the desired peptide chain is formed, the protecting groups are removed from the different amino acids constituting the peptide chain and the peptide is cleaved from the resin, for example, with the aid of hydrogen fluoride.

The peptide thus obtained can be purified, for example by means of column chromatography.

The SMR1 peptide or derivatives of this peptide can also be obtained with the aid of the techniques of genetic engineering; they can also be obtained by purification from biological material by means of techniques of chromatography or precipitation similar to those used, for example, for the purification of human growth hormone starting from the hypophysis.

The monoclonal and polyclonal sera can be prepared according to a standard technique. For this purpose the tetrapeptides or the pentapeptides or multimeric derivatives of these peptides can be coupled to immunogenic agents such as KLH (Keyhole Lympet Hemocyanin), ovalbumin, bovine serumalbumin etc, by a coupling agent such as glutaraldehyde. The SMR1 protein and the derivatives of this protein (peptides derived from this protein, or hybrid proteins containing a part or all of SMR1 linked to another protein such as protein A) can also be injected directly.

The immunizations can be performed in a standard manner, for example, in the rabbit and the mouse by injecting into the animal 100 micrograms, for example, of the coupling product in the presence of Freund's adjuvant 3 to 4 times at intervals of 3 weeks. It is thus possible to obtain polyclonal sera in the rabbit.

The hybridomas and the monoclonal antibodies can be obtained by means of the standard procedures.

The isolation of the mRNA, which corresponds to the SMR1 polypeptide, and the properties of the polypeptide and the maturation products will be described in more detail below.

1) Materials and Methods

Animals and Hormonal Treatments 10 weeks old male and female Wistar rats were obtained from Iffa-Credo. The androgens were removed by castration and 10 days later 35 mg of testosterone (Sterandryl retard, Roussel) were injected by the intraperitoneal route in the cases indicated. In the cases indicated, the same dose of testosterone was administered to female rats. 8 weeks old DBA/2 and "Swiss" mice were obtained from the Pasteur Institute.

Extraction of the RNA and In Vvitro Translation

The RNA was prepared from rat and mouse tissues as described in the literature (Tronik D. et al. 1987, EMBO J. 6, 983–987). The in vitro translation of the RNAs was carried out by using the mRNA-dependent translation system as a lysate in the presence of mRNA-dependent reticulocytes (Pelham H. RB et al., 1976, Eur. J. Biochem. 67, 247–256). The products were analysed by electrophoresis on a denaturing polyacrylamide-NaDodSO$_4$ gel.

Cloning and Characterization of the cDNA Coding for SMR1

Poly(A) RNA obtained from SMG of male Wistar rats was used as matrix for the reverse transcriptase, and the double-stranded cDNAs were obtained by means of the DNA synthesis system of Amersham, with the protocol supplied by the manufacturer. The double-stranded cDNA was then inserted into the PstI site of pUC9 by the method of the oligo-d(C) ends (Maniatis, T. et al. (1982) in Molecular Cloning: A Laboratory Manual (Cold Spring Harbor Laboratory, Cold Spring Harbor, N.Y.) pp 241–242). The host bacteria (bacterial strain DH 5-1 derived from DH1 and yielding high efficiencies of transformation, see Hanatian DNA cloning vol. 1, p. 111) were transformed and the colonies were screened by hybridization with the probes described below. In brief, the mRNA derived from the SMG of males and females was fractionated in a 5–20% sucrose gradient. The fractions enriched in mRNA of low molecular weight (which were shown by in vitro translation to contain the mRNA coding for SMR1) were precipitated with ethanol, and they were used as matrix for the reverse transcriptase in the presence of dGTP and dCTP radiolabelled with $^{32}$P. About 3000 recombinants were screened on filters in duplicate samples with the radiolabelled cDNA obtained from the SMG of male and female rats. The clones selected demonstrated a strong hybridization with the male cDNA probe but a very weak hybridization with the female probe. The recombinant clones were identified by experiments of inhibition of translation of the mRNAs in a cell-free system by DNA-mRNA hybridization (Paterson et al. (1977) Proc. Natl. Acad. Sci. USA, 74, 4370–4374).

Sequencing of the cDNA Coding for SMR1

With the aid of various restriction enzymes, the cDNA coding for SMR1 was cut and the fragments obtained were subcloned in the vector M13 mp9. The sequencing of the DNA was carried out by means of the method of termination with dideoxyribonucleotides (Sanger, F. et al. (1977) Proc. Natl. Acad. Sci. USA, 74, 5463–5467).

2) Results
Analysis of the In Vitro Translation of mRNA Prepared from the SMG of Rats and Mice.

5 μg of total RNA obtained from the SMG of male and female mice or male and female rats were translated in a cell-free system of reticulocytes in the presence of $^{35}$S-methionine. The products of in vitro translation were subjected to electrophoresis on a 12.5% sodium dodecylsulfate-polyacrylamide gel and autoradiographed.

The comparison of the products of the in vitro translation of RNA prepared from the SMG of male and female rats shows the presence of several polypeptide (of apparent molecular weights of 18,000, 19,000, 35,000, 46,000) in larger amounts in the male rats than in the females. These data show the existence of a sexual dimorphism in the SMG of the rat.

Furthermore, the comparison of these products of translation with those obtained with RNAs derived from SMG of mice shows that most of the major polypeptide are different in the two species. In particular, whereas sex-linked differences could also be observed in the mouse, these latter did not relate to the same polypeptide as in the rat. Conversely, the products of translation observed in the rat to be specific for the male seem to be absent in the mouse.

Isolation and Sequence of a cDNA Complementary to a specific mRNA of the Male Rat In order to isolate mRNAs specific for the male from the SMG of the rat, a bank of cDNA prepared from this tissue was constructed in pUC9. The recombinant clones were screened by utilizing a differential screening strategy such as that described in the Materials and Methods section. The positive clones were characterized by experiments of inhibition of translation of the mRNAs in a cell system by DNA-mRNA hybridization. One category of recombinant cDNAs suppressed the in vitro synthesis of a polypeptide having an apparent molecular weight of 19,000 daltons. This polypeptide, designated SMR1, is present in the products of in vitro translation of RNAs from male rats but is not present in those from females. The corresponding cDNA was utilized as probe in RNA hybridization experiments with transfer to a nitrocellulose membrane. For the hybridization a solution was used containing:

0.5 M sodium phosphate, pH 7.2
7% sodium dodecylsulfate (SDS)
1 mM EDTA
1% bovine serum albumin
sonicated salmon sperm DNA: 100 mg/ml
The experiment was done at 65° C. for 16 to 20 h.
4 washings of 10 minutes each were carried out at 65° C. with a solution containing:
40 mM sodium phosphate, pH 7.2
1% SDS
1 mM EDTA The cDNA is hybridized with a mRNA 700 nucleotides long, present in large amounts in the SMG of male rats. This inserted element of cDNA has been characterized in more detail.

The sequence of the cDNA coding for SMR1 and the sequence deduced for the protein are represented below (SEQ ID NOS: 7–8),

```
                    AAA CTG ACT CAC CAC ACA CCT TCT CAC CAC CAC ATT TCC CCG CTC AGA ACT TTC     54

1
                                  Met Lys Ser Leu Tyr Leu Ile Phe Gly Leu Trp Ile            108
                    TCC AAG CGG CTA CCA AAG ATG AAG TCA CTG TAT TTG ATC TTT GGC CTG TGG ATC 20                                    30
                    Leu Leu Ala Cys Phe Gln Ser Gly Glu Gly Val Arg Gly Pro|Arg Arg Gln His   162
                    CTT CTA GCA TGC TTC CAG TCA CCT CAG GGT GTC AGA GGC CCA AGA AGA CAA CAT

40
                    Asn Pro Arg Arg|Gln Gln Asp Pro Ser Thr Leu Pro His Tyr Leu Gly Leu Gln   216
                    AAT CCT AGA AGA CAA CAA CAT CCT TCA ACT CTT CCT CAT TAT CTT CCT CTT CAC 50                                              60
                    Pro Asp Pro Asn Gly Gly Gln Ile Gly Val Thr Ile Thr Ile Pro Leu Asn Leu   270
                    CCT GAT CCC AAT CGT CGA CAA ATA CGA GTA ACA ATC ACT ATA CCC TTA AAT CTT 70                                              80
                    Gln Pro Pro Arg Val Leu Val Asn Leu Pro Gly Phe Ile Thr Gly Pro Pro Leu   324
                    CAA CCA CCT CGT GTT GTT GTT AAT CTT CCC CGT TTT ATC ACT GGA CCA CCA TTG 90                                          100
                    Val Val Gln Gly Thr Thr Glu Tyr Gln Tyr Gln Trp Gln Leu Thr Ala Pro Asp   378
                    CTT GTA CAA CGT ACC ACT CAA TAT CAA TAT CAG TGG CAG CTA ACT CCT CCA CAC 110                                 120
                    Pro Thr Pro Leu Ser Asn Pro Pro Thr Gln Leu His Ser Thr Glu Gln Ala Asn   432
                    CCT ACA CCT CTA AGC AAT CCT CCT ACT CAA CTT CAT TCC ACA GAA CAA CCA AAT

*   130                         *
                    Thr Lys Thr Asp Ala Lys Ile Ser Asn Thr Thr Ala Thr Thr Gln Asn Ser Thr   486
                    ACA AAA ACA CAT CCC AAA ATC TCC AAC ACT ACT CCG ACT ACC CAA AAT TCC ACT

140
                    Asp Ile Phe Glu Gly Gly Gly Lys                                           549
                    CAT ATT TTT GAA CCT CGT CCC AAA TAATAAATTCCTTTTCCCACTTACAATACCATAAATCAA

AACACTGTCTACTTTTCCCCCAAATAATCTTTAAACCCTTCACAAACAACCTTTACCCCCATTATACAAAA   620

TCACAATAAACACCTAACCACCATTACACACCAAAAAA                                    658
```

The inserted cDNA has a length of 652 nucleotides, if the poly(A) fragment is excluded. This sequence comprises an open reading frame of 510 nucleotides. The only ATG which can serve as initiation codon is situated 73 nucleotides downstream from the 5' end of the clone of cDNA. The untranslated region at the 3' end (142 nucleotides long) contains the consensus signal for polyadenylation (AATAAA), 23 nucleotides upstream from the poly(A) tail (nucleotides 625–630). The translation stop codon is found in another AATAAA sequence (512–517) which apparently is not recognized as polyadenylation signal.

The corresponding protein has a length of 146 amino acids, which corresponds to a molecular weight of about 16,000 daltons. This molecular weight is slightly lower than that determined from the electrophoretic mobility of the in vitro translation product (19,000 daltons). Such a difference between the molecular weight calculated from the analysis of the sequence and that determined from the electrophoretic mobility has already been described for other proteins of the SMG of the rat or the mouse.

SMR1 has a relatively high content of glutamine and proline residues, but does not contain a repetitive region. Hence, it does not belong to the family of polypeptide "rich in proline" or "rich in glutamine", which are essential proteins of the SMG. Furthermore, the sequence of the mRNA does not contain at its 5' end the sequence of 80 nucleotides which is characteristic of this family. However, like these proteins, SMR1 does not contain cystein or methionine residues (except in its signal peptide).

The amino-terminal part of SMR1 is strongly hydrophobic, which is characteristic of signal peptides of most of the secreted proteins. Although the amino-terminal sequence of the mature protein has not been determined directly, from the statistical analysis made according to G. Von Heijne (Nucleic Acids Res. 14, 4683–4690, 1986) (rule "–3,–1"), it may be supposed that the cleavage site of the signal peptide is located between the residues 18 and 19.

The protein SMR1 also shows certain features characteristic of the glycoproteins. The presence of two potential glycosylation sites linked to N are observed at the positions 139 and 136. The protein is relatively rich in proline (12%), threonine (12%) and glutamine (9.5%). Several glycosylation sites linked to 0 might thus be present in the carboxy-terminal fragment of SMR1, since regions rich in proline and threonine residues are usually present in highly O-glycosylated proteins, such as the mucoproteins and the sialoglyco-proteins.

An interesting characteristic is the presence of pairs of basic ammo acids Arg-Arg at positions 27–28 and 33–34. Such dipeptides represent potential sites of cleavage by maturation enzymes (Lazure. C., et al (1983) Can. J. Biochem., Cell Biol. 61, 501–515 and Docherty, K. et al (1982) Ann. Rev. Physiol. 44, 625–638). They flank a tetrapeptide Gln-His-Asn-Pro (SEQ ID NO: 1). The tetrapeptides and its adjacent sequences are located in a hydrophilic environment which renders this region accessible to possible maturation enzymes.

The cleavage of Arg-Arg linkages by a maturation enzyme followed by the removal of the basic residues by carboxypeptidase E (Fricker. L.D. et al (1983) J. Dial. Chem. 258, 10950–10955) and possibly an aminopeptidase (Loll, Y.P. et al (1984) Ann. Rev. Neurosci. 7, 189–222) would produce a mixture of tetrapeptide (Gln-His-Asn-Pro (SEQ ID No: 1) and pentapeptide (Gln-His-Asn-Pro-Arg (SEQ ID NO: 3)), since "Pro-Arg" is not a good substrate for carboxypeptidase E. Other post-translational modifications could also include the formation of pyroGlu acid derivatives of these products, giving rise to a mixture of pyroGlu-His-Asn-Pro-Arg (SEQ ID NO: 4) and pyroGlu-His-Asn-Pro (SEQ ID No: 2). These structures recall those of thyroliberin (TRH).

Regulation of the Accumulation of mRNA Coding for SMR1 in the SMG of the Rat by Androgens.

In order to study the regulation of the accumulation of mRNA coding for SMR1 in the SMG of the rat by androgens, mRNA containing a poly(A) sequence was prepared from the SMG of adult males, males castrated 20 days previously, castrated males subjected to a treatment with androgens, females and females treated with androgens. 1 µg of total RNA from male rats, female rats treated with testosterone, castrated male rats, castrated male rats treated with testosterone and female rats was subjected to electrophoresis in a 1.4% agarose-formaldehyde gel, these RNAs were transferred to a Nylon membrane and were hybridized with the cDNA probe coding for SMR1. The time of exposure for autoradiography was 2 hours. The results of the RNA analysis, by transfer of these mRNAs to solid supports, by means of a SMR1 probe labelled with $^{32}P$ are shown in the figure (part A). A considerable difference in the accumulation of mRNA coding for SMR1 is observed in the SMG of male rats and those of females.

Furthermore, various amounts (as indicated in the figure) of RNA from the SMG of male rats and female rats were subjected to electrophoresis on a 2% agarose-formaldehyde gel, they were transferred to filters and hybridized with the cDNA probe coding for SMR1. The film was exposed for 30 hours. As is apparent in part B, the mRNA coding for SMR1 accumulates in very large quantities in the SMG of male Wistar rats, since an amount as low as 1.5 ng of total RNA was sufficient to give a hybridization signal. Conversely, the level of accumulation of mRNA coding for SMR1 in the SMG of female Wistar rats was about 1,000 to 3,000 times lower than that in males.

In the castrated males, the quantity of mRNA coding for SMR1 was reduced 10 to 20 fold. The administration of testosterone to these males restored the amount of mRNA coding for SMR1 to the same value as that observed in the non-castrated males. Furthermore, the administration of testosterone to adult female rats caused the accumulation of mRNA coding for SMR1 in amounts similar to that observed in the males.

A remarkable property of the mRNA coding for SMR1 is its high degree of accumulation in the SMG of the rat in response to a treatment with androgens. This strongly suggests that SMR1 is synthesized in the GCT cells of the SMG (just like the EGF, NGF and renin as well as other proteins under the control of androgens in the SMG of the mouse). Furthermore, the difference in the level of accumulation of mRNA coding for SMR1 in the male and in the female is very great(greater than three orders of magnitude), in comparison with that usually observed for other genes controlled by antigens in the target organs (kidney, liver, SMG).

These results, and in particular the high degree of induction of the SMR1 gene by androgens, suggest that SMR1 may fulfil an important function specific for the male in the rat. SMR1 might be the precursor of a molecule (the tetra- or pentapeptides or the C-terminal part of SMR1) controlling behavioural characteristics in the male rat.

The products described in the present invention can be used for therapeutic purposes or as laboratory reagents.

What is claimed is:

1. A method for detecting and/or quantifying a nucleic acid coding for submandibular/submaxillary rat 1 protein (SMR1) comprising:

a) contacting a DNA or RNA molecule with a nucleotide probe having the nucleotide sequence of nucleotides 1 to 510 of SEQ ID NO: 7 in a hybridization solution containing 0.5 M sodium phosphate, pH 7.2,
    7% sodium dodecylsulfate,
    1 mM EDTA,
    1% bovine serum albumin, and
    sonicated salmon sperm DNA: 100 mg/ml, at 65° C. for 16 to 20 h so as to allow said probe to hybridize with the target DNA or RNA molecule, washing four times for 10 minutes at 65° C. with a solution containing 40 mM sodium phosphate. DH 7.2
    1% sodium dodecylsulfate
    1 mM EDTA; and b) detecting the hybrid formed between the DNA or RNA molecule and said nucleotide probe.

2. A method according to claim 1 for detecting and/or qualifying mRNA coding for SMR1 polypeptide consisting essentially of:

a) preparing mRNAs containing poly (A) sequence from the sub-maxillary gland of a rat;

b) subjecting said RNAs prepared in step a) to an electrophoresis in a gel;

c) transferring said RNAs to a nitrocellulose membrane;

d) contacting said membrane with a nucleotide probe having the nucleotide sequence of nucleotides 1 to 510 of SEQ ID NO: 7 said probe to hybridize to the target RNA, washing four times for 10 minutes at 65° C. with a solution containing 40 mM sodium phosphate, pH 7.2

1% sodium dodecylsulfate 1 mM EDTA;

e) detecting the hybrid formed between the RNA and the nucleotide probe; and f) optionally quantifying the number of hybrid molecules as formed.

* * * * *

SEQUENCE LISTING (1) GENERAL INFORMATION:

(iii) NUMBER OF SEQUENCES: 8

(2) INFORMATION FOR SEQ ID NO: 1:

(i) SEQUENCE CHARACTERISTICS:
          (A) LENGTH: 4 amino acids
          (B) TYPE: amino acid
          (C) STRANDEDNESS: Not Relevant
          (D) TOPOLOGY: Not Relevant (ii) MOLECULE TYPE: peptide (xi) SEQUENCE DESCRIPTION: SEQ ID NO: 1:

Gln His Asn Pro (2) INFORMATION FOR SEQ ID NO: 2:

(i) SEQUENCE CHARACTERISTICS:
          (A) LENGTH: 4 amino acids
          (B) TYPE: amino acid
          (C) STRANDEDNESS: Not Relevant
          (D) TOPOLOGY: Not Relevant (ii) MOLECULE TYPE: peptide (xi) SEQUENCE DESCRIPTION: SEQ ID NO: 2:

Xaa His Asn Pro (2) INFORMATION FOR SEQ ID NO: 3:

(i) SEQUENCE CHARACTERISTICS:
          (A) LENGTH: 5 amino acids
          (B) TYPE: amino acid
          (C) STRANDEDNESS: Not Relevant
          (D) TOPOLOGY: Not Relevant (ii) MOLECULE TYPE: peptide (xi) SEQUENCE DESCRIPTION: SEQ ID NO: 3:

Gln His Asn Pro Arg
                 5

(2) INFORMATION FOR SEQ ID NO: 4:

(i) SEQUENCE CHARACTERISTICS:
          (A) LENGTH: 5 amino acids
          (B) TYPE: amino acid
          (C) STRANDEDNESS: Not Relevant
          (D) TOPOLOGY: Not Relevant (ii) MOLECULE TYPE: peptide (xi) SEQUENCE DESCRIPTION: SEQ ID NO: 4:

Xaa His Asn Pro Arg
                 5

(2) INFORMATION FOR SEQ ID NO: 5:

(i) SEQUENCE CHARACTERISTICS:
          (A) LENGTH: 5 amino acids
          (B) TYPE: amino acid
          (C) STRANDEDNESS: Not Relevant
          (D) TOPOLOGY: Not Relevant (ii) MOLECULE TYPE: peptide (xi) SEQUENCE DESCRIPTION: SEQ ID NO: 5:

Gln His Asn Pro Lys
                 5

(2) INFORMATION FOR SEQ ID NO: 6:

(i) SEQUENCE CHARACTERISTICS:
        (A) LENGTH: 5 amino acids
        (B) TYPE: amino acid
        (C) STRANDEDNESS: Not Relevant
        (D) TOPOLOGY: Not Relevant (ii) MOLECULE TYPE: peptide (xi) SEQUENCE DESCRIPTION: SEQ ID NO: 6:

Xaa His Asn Pro Lys
                 5

(2) INFORMATION FOR SEQ ID NO: 7:

(i) SEQUENCE CHARACTERISTICS:
        (A) LENGTH: 658 base pairs
        (B) TYPE: nucleic acid
        (C) STRANDEDNESS: Not Relevant
        (D) TOPOLOGY: Not Relevant (ii) MOLECULE TYPE: cDNA (vi) ORIGINAL SOURCE:
        (A) ORGANISM: Rat
        (F) TISSUE TYPE: Submaxillary Gland
        (G) CELL TYPE: Glandular (viii) POSITION IN GENOME:
        (A) CHROMOSOME/SEGMENT: SMR1

(ix) FEATURE:
        (A) NAME/KEY: CDS
        (B) LOCATION: 73..510

(xi) SEQUENCE DESCRIPTION: SEQ ID NO: 7:

```
AAACTGACTG ACCAGAGAGC TTCTGACCAG CACATTTCCC CGCTCAGAAG TTTCTCCAAG      60

GGGCTACCAA AG ATG AAG TCA CTG TAT TTG ATC TTT GGC CTG TGG ATC         108
              Met Lys Ser Leu Tyr Leu Ile Phe Gly Leu Trp Ile
                1               5                       10

CTT CTA GCA TGC TTC CAG TCA GGT GAG GGT GTC AGA GGC CCA AGA AGA       156
Leu Leu Ala Cys Phe Gln Ser Gly Glu Gly Val Arg Gly Pro Arg Arg
            15                  20                  25

CAA CAT AAT CCT AGA AGA CAA CAA GAT CCT TCA ACT CTT CCT CAT TAT       204
Gln His Asn Pro Arg Arg Gln Gln Asp Pro Ser Thr Leu Pro His Tyr
        30                  35                  40

CTT GGT CTT CAG CCT GAT CCC AAT GGT GGA CAA ATA GGA GTA ACA ATC       252
Leu Gly Leu Gln Pro Asp Pro Asn Gly Gly Gln Ile Gly Val Thr Ile
45                  50                  55                  60

ACT ATA CCC TTA AAT CTT CAA CCA CCT CGT GTT CTT GTT AAT CTT CCC       300
Thr Ile Pro Leu Asn Leu Gln Pro Pro Arg Val Leu Val Asn Leu Pro
                65                  70                  75

GGT TTT ATC ACT GGA CCA CCA TTG GTT GTA CAA GGT ACC ACT GAA TAT       348
Gly Phe Ile Thr Gly Pro Pro Leu Val Val Gln Gly Thr Thr Glu Tyr
            80                  85                  90

CAA TAT CAG TGG CAG CTA ACT GCT CCA GAC CCT ACA CCT CTA AGC AAT       396
Gln Tyr Gln Trp Gln Leu Thr Ala Pro Asp Pro Thr Pro Leu Ser Asn
        95                  100                 105
```

-continued

| | | | | | | | | | | | | | | | |
|---|---|---|---|---|---|---|---|---|---|---|---|---|---|---|---|
| CCT | CCT | ACT | CAA | CTT | CAT | TCC | ACA | GAA | CAA | GCA | AAT | ACA | AAA | ACA | GAT | 444 |
| Pro | Pro | Thr | Gln | Leu | His | Ser | Thr | Glu | Gln | Ala | Asn | Thr | Lys | Thr | Asp |
| | 110 | | | | 115 | | | | | 120 | | | | | |

| GCC | AAA | ATC | TCC | AAC | ACT | ACT | GCG | ACT | ACC | CAA | AAT | TCC | ACT | GAT | ATT | 492 |
| Ala | Lys | Ile | Ser | Asn | Thr | Thr | Ala | Thr | Thr | Gln | Asn | Ser | Thr | Asp | Ile |
| 125 | | | | | 130 | | | | | 135 | | | | | 140 |

| TTT | GAA | GGT | GGT | GGC | AAA | TAATAAATTC | CTTTTGGCAG | TTACAATAGC | 540 |
| Phe | Glu | Gly | Gly | Gly | Lys |
| | | | | 145 |

ATAAATCAAA ACACTGTCTA GTTTTGGCCG AAATAATCTT TAAAGGCTTG AGAAACAACC    600

TTTACCCCCA TTATAGAAAA TGACAATAAA GAGCTAAGCA GCATTACACA GCAAAAAA     658

(2) INFORMATION FOR SEQ ID NO: 8:

(i) SEQUENCE CHARACTERISTICS:
        (A) LENGTH: 146 amino acids
        (B) TYPE: amino acid
        (D) TOPOLOGY: linear (ii) MOLECULE TYPE: protein (xi) SEQUENCE DESCRIPTION: SEQ ID NO: 8:

Met Lys Ser Leu Tyr Leu Ile Phe Gly Leu Trp Ile Leu Leu Ala Cys
 1               5                  10                  15

Phe Gln Ser Gly Glu Gly Val Arg Gly Pro Arg Arg Gln His Asn Pro
            20                  25                  30

Arg Arg Gln Gln Asp Pro Ser Thr Leu Pro His Tyr Leu Gly Leu Gln
        35                  40                  45

Pro Asp Pro Asn Gly Gly Gln Ile Gly Val Thr Ile Thr Ile Pro Leu
    50                  55                  60

Asn Leu Gln Pro Pro Arg Val Leu Val Asn Leu Pro Gly Phe Ile Thr
65                  70                  75                  80

Gly Pro Pro Leu Val Val Gln Gly Thr Thr Glu Tyr Gln Tyr Gln Trp
            85                  90                  95

Gln Leu Thr Ala Pro Asp Pro Thr Pro Leu Ser Asn Pro Pro Thr Gln
            100                 105                 110

Leu His Ser Thr Glu Gln Ala Asn Thr Lys Thr Asp Ala Lys Ile Ser
        115                 120                 125

Asn Thr Thr Ala Thr Thr Gln Asn Ser Thr Asp Ile Phe Glu Gly Gly
    130                 135                 140

Gly Lys
145